(12) United States Patent
Barinova et al.

(10) Patent No.: US 6,607,715 B1
(45) Date of Patent: Aug. 19, 2003

(54) FATTY AMMONIUM QUATERNARY COMPOSITIONS

(75) Inventors: Helena S. Barinova, Iselin, NJ (US); Kostas Nikolopoulos, Piscataway, NJ (US); Abel G. Pereira, Belleville, NJ (US)

(73) Assignee: Croda, Inc., Parsippany, NJ (US)

( * ) Notice: Subject to any disclaimer, the term of this patent is extended or adjusted under 35 U.S.C. 154(b) by 0 days.

(21) Appl. No.: 09/438,631

(22) Filed: Nov. 12, 1999

Related U.S. Application Data

(60) Provisional application No. 60/107,983, filed on Nov. 12, 1998.

(51) Int. Cl.$^7$ ............................. A61K 7/06; A61K 31/74
(52) U.S. Cl. .................. 424/70.1; 424/70.27; 424/70.28
(58) Field of Search ........................... 424/70.1, 70.27, 424/70.28

(56) References Cited

U.S. PATENT DOCUMENTS

| | | | |
|---|---|---|---|
| 4,436,722 A | * | 3/1984 | Matsunaga et al. |
| 4,818,523 A | * | 4/1989 | Clarke et al. |
| 4,891,214 A | | 1/1990 | Stevens et al. |
| 5,284,650 A | * | 2/1994 | Whittlinger |
| 5,635,469 A | | 6/1997 | Fowler et al. ............... 510/460 |
| 5,683,685 A | | 11/1997 | Hirano et al. ............. 424/78.03 |
| 5,683,973 A | * | 11/1997 | Post et al. |

FOREIGN PATENT DOCUMENTS

WO    WO-96/06595 A1  *  3/1996

* cited by examiner

*Primary Examiner*—Thurman K. Page
*Assistant Examiner*—Todd D Ware
(74) *Attorney, Agent, or Firm*—Lerner, David, Littenberg, Krumholz & Mentlik, LLP

(57) ABSTRACT

The invention relates to a commercially feasible fatty ammonium quat compound or composition useful in hair products and the like comprising the properties of being flakeable and having at least 35% cationic activity.

30 Claims, No Drawings

FATTY AMMONIUM QUATERNARY COMPOSITIONS

CROSS REFERENCE

This application claims priority from U.S. Provisional Application, Serial No. 60/107,983, filed on Nov. 12, 1998. The contents of that Application are hereby incorporated by reference herein.

FIELD OF THE INVENTION

The invention relates to the fields of chemistry and personal care products and provides additives which are useful and convenient for formulating shampoos, conditioners and the like, as well as methods of providing same.

BACKGROUND OF THE INVENTION

Fatty ammonium quaternary compositions (hereinafter "quats") are useful additives to hair care products such as shampoos, conditioners and the like. U.S. Pat. No. 4,891,214 issuing to Stevens et al. on Jan. 2, 1990 provides an informative background into quats and their uses.

In the hair care industry, it is desirable to provide quats in compounds and formulations having a high cationic activity (i.e. relative high concentration of quats to water/solvent mixture). It is also desirable to produce compounds and formulations that, in addition to having a high cationic activity, provide for ease in commercial handling and storage. This is easier said than done. Quats, to be most useful as an additive, should be in the form of a flakeable solid. For the purposes of this application, the term "flakeable" is used to describe the products of processes such as flaking and pastillation.

Achieving the desired high cationic activity while maintaining the product in the liquid state is generally not feasible. Even in the case of compositions using a relatively short chain quat (i.e. a $C_{16}$ (16 carbons) fatty chain monoalkyl quat), with water as a solvent, the maximum cationic activity is about 30%. This is the limit for most quats in the liquid state. The cationic activity decreases significantly as the chain lengths increase. Further, the shipping and use of such dilute solutions of quats are undesirable. Finally, high volumes of materials will be required to obtain the necessary quat content in hair care products. This increases total volume, package size, weight, etc.

To boost the cationic activity, and therefore the quat content, other solvents have been tried. Mixtures of water and short chain normal alcohols, for example, produced improved results. Use with, for example, IPA (isopropyl alcohol) increased the cationic activity potential dramatically. In fact, with certain quats, cationic activities as high as about 85% could be realized.

While these products exhibit the desired cationic activity, the normal alcohols are volatile organic solvents (solvents with a boiling point of 85° or lower) which raise significant environmental and safety concerns, both for the consumer and for the company formulating the personal care product. This volatility makes these products less commercially viable. Therefore, it is desirable to find other, non-volatile solvent systems which exhibit the same potential for high cationic activities.

Another potential solvent system utilizes fatty alcohols as opposed to the volatile normal alcohol/water mixtures. Fatty alcohols do not share the same problem with volatility that plagues normal alcohol/water solvent mixtures. In fact, fatty alcohols such as cetearyl alcohol (a mixture of cetyl and stearyl alcohol) have been used as quat solvents. The use of fatty alcohols as solvents has a number of advantages. First of all, many hair care and cosmetic products would have included some amount of fatty alcohols anyway. Also, these quat formulations can be flakeable.

However, as one attempts to boost the effective cationic activity in the formulation, namely the amount of quat used, and as the chain length of the quats and/or the fatty alcohols used increases, so too do the handling problems. In order to effectively handle and, ultimately, flake the material, it must often be heated to a point near, or above, its melting point. This melting point is typically over 100° C. and at that temperature, the quat can begin to degrade. Viscosity also becomes a dramatic stumbling block to formulating end products. For example, using a quat raw material in a fatty alcohol solvent at about 25% cationic activity and assuming it was desired that the finished product would have a 1.5% effective cationic activity, one would need to use 6% by weight of the product (1.5% divided by 0.25 equals 6%). At that level, the relatively high content of fatty alcohol tends to dramatically increase the viscosity of the finished product.

The viscosity/handling problems significantly increase the costs associated with using fatty alcohols as a solvent and the effectiveness of the resulting product. This effectively renders the use of fatty alcohols as a solvent not commercially feasible.

These problems are further complicated at higher cationic activities, longer chain fatty alcohols and/or longer chain fatty quats. These complications, coupled with the addition of other traditional additives to personal care products including emollients and conditioners typically have a further negative impact on commercial handling properties. Their addition in combination with the alcohol/quat mixture will only exacerbate the problem.

Thus, as can be readily understood, while fatty alcohols can provide the desired cationic activities, they do so at the expense of commercial feasibility due to the described viscosity/handling problems.

Another potential solvent system is one comprised of glycols. Glycols such as low molecular weight, short chain alkylene glycols, both normal and branched, can be effective solvents. Glycols offer several advantages. Specifically, they allow for relatively higher concentrations of cationic activity, a lower melting point than the fatty alcohol solvent systems, and do not tend to elevate the viscosity undesirably, at least not to a level comparable to the fatty acids.

However, glycols also have a number of drawbacks. First, quats containing glycols as a solvent generally result in formulations which are not flakeable. Instead, they form a somewhat viscous, waxy, "gummy" solid. While this material may have a lower overall melting point than the fatty alcohol based solvent quats, the overall handling problems involved from this material are significantly greater.

In particular, a drum of this material would most likely require heating for several hours or even days under moderate heat to place it in a state where it can be pumped and handled. The material must then be melted further to a usable form taking time and considerable cost in energy. Flakes, on the other hand, can merely be dumped into a vat and are easier to handle, measure and the like.

In sum, each attempt to increase the cationic activity while obtaining desirable commercial handling properties falls short in one aspect or another. Use of water as a solvent results in low cationic activity. Use of normal alcohols as a solvent results in high organic volatility. Use of fatty alcohols as a solvent results in viscosity problems which require heating the resulting product to a point in which the quats begin to degrade. Use of glycols as a solvent results in a product which is not flakeable. Until now, there existed no quat compound or composition which exhibits all of the favorable properties described above.

SUMMARY OF THE INVENTION

It has been discovered that by producing a solvent mixture of fatty alcohols and glycols, one can achieve many of the advantages of both without many of the disadvantages realized by the use of either. This is contrary to the common understanding that both fatty alcohols and glycols, when used by themselves, as solvents exhibit substantial commercial handling problems.

Utilizing the mixture of fatty alcohols and glycols as a solvent according to the present invention, one can achieve higher cationic activities. For a $C_{16}$ fatty quat, for example, one can obtain cationic activities as high as 50 or 60%. At longer fatty chain length based quats, 40 to 50% activity may be the maximum.

In addition, quats containing a mixture of fatty alcohols and glycols as a solvent generally result in formulations which are flakeable. The melting point of the resulting flakeable material is also generally low enough that it can be melted conveniently without a likelihood of damaging the quat. Most preferably, this can be done at commercially viable temperatures and without the need for expensive processing such as pressurized vessels.

Thus, the end result is a flakeable material with increased cationic activity which still may be easily handled, just as fatty alcohol based materials, without the risk of decomposition of the quat.

According to the present invention, a quat compound is contemplated. The properties of the quat/solvent mixture include at least 35% cationic activity and being flakeable. Preferably, this mixture has a melting point below the point at which the quat begins to degrade or break down.

The quat composition contemplated generally includes an amount of fatty ammonium quat distributed in a solvent. The solvent used has at least one fatty alcohol and at least one glycol and the resulting mixture has at least 35% cationic activity, while at the same time being flakeable.

According to a preferred aspect of the present invention, a fatty ammonium quaternary composition is contemplated. The composition includes a fatty ammonium monoalkyl quat that includes at least one fatty chain of between about 12 and about 36 carbons in length, distributed in a solvent. The solvent used is a mixture of at least one fatty alcohol, with a chain length of 12 to 24 carbons, and at least one glycol. The amount of the fatty alcohol in the solvent mixture is greater than the amount of the glycol in the mixture.

DETAILED DESCRIPTION OF THE PREFERRED EMBODIMENTS

The general structures for fatty ammonium monoalkyl quats contemplated by the present invention are:

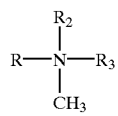

FIG. 1

Where: R=(1) an alkyl chain of 12 to 36 carbons, (2)$R_4CONH(CH_2)_n$

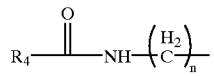

or (3)$R_4COO(CH_2)_n$

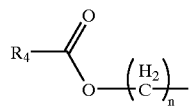

where:
  $R_4$=an alkyl chain of 12 to 36 carbons, and
  n=an integer from 1 to 8; and $R_2$ & $R_3$=a $CH_3$ or a $CH_3CH_2$ group.

Although any fatty ammonium monoalkyl quat may be used in accordance with the present invention, it is preferred that methyl quats, more preferrably trimethyl quats (quats with $R_2$ and $R_3$ being methyl groups) are used. As shown in FIG. 1 above, monoalkyl methyl quats, in accordance with the present invention, generally have a carbon chain length, R, of 12 and above, more preferably 16 and above, and often between about 16 and about 32. This group may also be an alkyl-amido ($R_4(2)$) or alkyl-ester group ($R_4(3)$). The other substituted positions, $R_2$ and $R_3$, are preferably either methyl or ethyl groups, more preferably both methyl groups. The $R_2$ and $R_3$ groups may also be substituted with non-polar species such as short chain alkyl or branched alkyl groups 1–8 carbons (substituted of unsubstituted), cyclic 1–8 carbons, unsaturated hydrocarbons (1–8 carbons, straight or branched, substituted or unsubstituted) or aryl (1–7 carbons, substituted or unsubstituted). Generally, groups like hydroxy groups, alkoxy, amine groups, thiols and halogen-substituted compounds, for example, would not be used although, under the right circumstances, some degree of increased polarity may be desirable.

Particularly preferred in accordance with the present invention are quats in which R is a behenyl ($C_{22:0}$) (i.e. 22 carbons with no unsaturation), erucic ($C_{22:1}$), cetyl ($C_{16:0}$) or stearyl ($C_{18:0}$) alkyl group. These would typically be substituted with short chain alkyl groups in which $R_2$ and $R_3$ are methyl, ethyl, propyl or butyl groups. Of course, not each position needs to be substituted with the same group.

Fatty alcohols used in accordance with this aspect of the present invention include lauryl ($C_{12:0}$), myristal ($C_{14:0}$), cetyl ($C_{16:0}$), stearyl ($C_{8:0}$), and behenyl ($C_{22:0}$) alcohols. Mixtures such as cetearyl alcohol mentioned previously, which are mixtures of cetyl and stearyl alcohols, are also useful. As a rule of thumb, pure alcohols such as cetyl alcohol tend to perform better than mixtures of alcohols such as cetearyl alcohol and the like. Therefore, it is preferable to use a substantially homogeneous fatty alcohol as a solvent. A substantially homogeneous fatty alcohol is an alcohol including less than approximately 10% by weight of another fatty alcohol.

Glycols in accordance with the present invention can include ethylene glycol, propylene glycol, butylene glycol, dipropylene glycol, polypropylene glycol, polyethylene glycol, etc. and mixtures thereof.

The content of the fatty ammonium monoalkyl quat in the solvent is, obviously, as high as possible while still maintaining the desired commercial handling properties. The amount will depend a great deal on the quat used as well as the specific solvent system selected. However, with generally lower fatty chain length quats, depending upon the solvent used, cationic activities can be as high as, for example, 60%. Preferably, the content of the quats will be at least about 35%, more preferably at least 50%.

The relative proportions of glycol and alcohol in the solvent depends somewhat on the quat used and more importantly on the specific alcohol/alcohols and glycol/glycols used.

Generally, the content of the fatty alcohol will be greater than the content of the glycol. Indeed, it is often desirable to minimize the amount of glycol used because an excess can provide an overly plastic quality to the resulting material. With that in mind, it is generally preferable that the solvent contains more fatty alcohol than glycol, more preferably at least about 60% by weight of fatty alcohol, more preferably at least about 75% by weight of fatty alcohol and most preferably at least about 85% by weight of fatty alcohol. However, there are circumstances where content of the fatty alcohol in the solvent can be as high as 95% by weight.

The fluidity of the composition is important from a manufacturing standpoint because without the proper final commercial handling properties, it will be extremely difficult to produce a commercially feasible product. During manufacture, the product has to be stirred, heated, cooled as needed, and often transferred in a fluid state to a flaking or pastillation line. All of this needs to be achieved at commercially viable temperatures, temperatures which will not degrade the quat.

Flakes or pastilles are desired in the commercial industry because they are easily handled and incorporated into desired products. If the product is gummy or pasty it will not be amenable to flaking or pastillation. Further, it will not often flow through the transfer line and will be difficult to heat or cool due to poor heat transfer.

In contrast, the claimed compositions are free-flowing liquids above their melting points, making them easy to manufacture and easy to transfer and pump through transfer lines to flaking or pastillation equipment where it is chilled below its melting point and either broken into easy to handle flakes or dispensed into pastilles and cooled. Thus, the claimed compositions generally require the melting point to be below 100° C. in order to facilitate the transfer to the flaking lines while maintaining the integrity of the quats in the composition. More preferably the melting point of the compositions is below 950° C., and most preferably the melting point of the compositions is below 90° C.

Whether a formulation is flakeable is measured by pouring a relatively thin film (1/16"–1/8") of the heated composition onto a metal sheet and allowing it to cool. The cooled film is then "crumbled" or "scraped" into small flakes by any type of mechanical process. Thus, a successful composition must possess two properties. First, the composition must possess the property of being easily poured onto the sheet, thus forming a thin film. Second, once the composition is allowed to cool, it must break into flakes after crumpling or scraping. These flakes are consequently easily stored and re-melted as necessary.

Pastillation is a process in which small amounts of the desired formulation are dispensed into pastilles. These pastilles are then allowed to cool, forming a product, which is in solid form, but easily returned to liquid state. Whether a formulation is capable of pastillation is measurable by distributing small amounts of the heated formulation into pastilles. These pastilles are then allowed to cool. The pastilles must be easily melted without tremendous amounts of heat, preferably below the boiling point of water.

Cationic activity is measured by several methods readily understood by those skilled in the art. One such method utilizes a standardized solution of an anionic material, such as sodium lauryl sulfate. This material is added to the solution containing the quat until full complexation of the quat's cations (the end point) has been reached. The end point can be measured potentiometrically or by the use of color indicators.

Typical tests involve titrating a sample of the quat, usually dissolved in a solvent, with the standardized solution of sodium lauryl sulfate until the endpoint is reached.

Once the endpoint is reached, the cationic activity can be calculated according to the following formula:

$$\% \text{ cationic activity} = \frac{mL \times N \times MW \times 100}{S. \text{ wt.} \times 1000}$$

Where: mL=the number of mL of anionic material
N=the normality of the solution used
MW=the molecular weight of the quat being analyzed
S.wt.=the sample weight in grams Once the desired solvent ratios have been determined for a given quat and solvent mixture, the compositions can then be produced by manufacturing the quat in situ using the fatty alcohol and glycol, as the solvent for the reaction mixture instead of volatile solvent. Generally, quaternizing of a tertiary amine is done using, for example, an alkyl tertiary amine and an alkylating agent such as methyl chloride, dimethyl sulfate, benzyl chloride and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

EXAMPLES

Example 1

Behenyl or Cetyl Trimethyl Ammonium Quats

Table 1 includes various formulations which were produced and tested for quat activity (cationic activity) and melting point. For testing purposes, the quat was produced in a volatile solvent and then the solvent was removed in a vacuum oven until the quat had approximately 97% activity. The quats used in this example were either a $C_{22}$ quat or a $C_{16}$ quat where, according to the formula listed above, R was either a behenyl alkyl chain ($C_{22}$) or a cetyl alkyl chain ($C_{16}$) and $R_2$ and $R_3$ were $CH_3$ groups. The formulations of the present invention were produced by mixing pure quat with fatty alcohol or fatty alcohol plus a glycol and heated until the products were melted. The temperature at which mixing can be accomplished and the fluidity of the composition was determined at that point. This example serves as a quick screening method.

TABLE 1

| Composition | Cationic Activity | Melting Point |
|---|---|---|
| $C_{14}$ Alcohol + $C_{22}$ Quat | 50% | 80° C.–82° C. |
| $C_{14}$ Alcohol (88%)* + Propylene Glycol (12%)* + $C_{22}$ Quat | 50% | 70° C.–72° C. |
| $C_{22}$ Alcohol + $C_{16}$ Quat | 50% | 84° C.–86° C. |
| $C_{22}$ Alcohol (76%)* + Propylene Glycol (24%)* + $C_{16}$ Quat | 50% | 74° C.–75° C. |

*percent by weight

The two formulations of the present invention, illustrated in table 1, demonstrate that with either relatively long chain length fatty alcohols or relatively long chain fatty quats, when mixed with propylene glycol, significant cationic activity, activity similar to that obtained without propylene glycol, can be achieved. However, in each case, the melting points of the formulations of the present invention were significantly lowered. Moreover, the viscosities of the formulations were particularly important. The compositions without propylene glycol were not fluid enough to be practical in manufacturing. They had a viscous, sticky consistency versus the free flowing liquids that resulted from the formulations of the present invention including propylene glycol. This consistency prohibited the compositions from being flakeable.

Example 2

Behenyl Trimethyl Ammonium Quats

Table 2 shows the resulting cationic activity, melting points and handling properties for various amounts and combinations of fatty alcohols, glycols and quats compiled during the preparation of behenyl trimethyl ammonium methosulfate and behenyl trimethyl ammonium chloride. The difference between the methosulfate quat and the chloride quat is the anion used in the preparation of the quat and is not particularly crucial to the present invention. The composition in this example is comprised of varying amounts of $C_{22}$ quat, where R was a behenyl alkyl chain and $R_2$ and $R_3$ were methyl groups, and varying amounts of cetearyl or cetyl alcohol. The composition utilizing $C_{22}$ methosulfate quat, cetyl alcohol (91%) and 1,3 butane diol (9%) produced the best composition exhibiting all of the desirable properties including cationic activity greater than 35%, being flakeable and exhibiting a low melting point, which translates to a commercially feasible composition. Any melting point greater than 100° C. is generally not commercially feasible (NCF) due to the problems of quat degradation described above, the increased expense in melting (as this is above the boiling point of water) and the difficulties in handling these compositions below the melting point.

TABLE 2

| | Composition | Cationic Activity | Melting Point/ Handling Properties |
|---|---|---|---|
| A | $C_{22}$ Methosulfate Quat + Cetearyl Alcohol (100%)* | 49.5% | 104–107° C. Flakeable - NCF |
| B | $C_{22}$ Methosulfate Quat + Cetearyl Alcohol (90.8%)* + 1,3 Butane Diol (9.2%)* | 40% | 64–67° C. Not Flakeable (Gummy) |
| C | $C_{22}$ Methosulfate Quat + Cetearyl Alcohol (90.8%)* + 1,3 Butane Diol (9.2%)* | 35.5% | 62–65° C. Flakeable |
| D | ◆$C_{22}$ Methosulfate Quat + Cetyl Alcohol (91%)* + 1,3 Butane Diol (9%)* | 49% | 84–86° C. Flakeable |
| E | $C_{22}$ Chloride Quat + Cetearyl Alcohol (100%)* | 49% | 105–108° C. Flakeable - NCF |
| F | $C_{22}$ Methosulfate Quat + Cetyl Alcohol (90%)* + 1,3 Butane Diol (10%)* | 48.8% | 84–86° C. Flakeable |

*percent by weight
◆optimal solvent/quat composition

The table above exemplifies several aspects of the present invention. In the first entry (A), no glycol was added to the fatty alcohol solvent. The result was a flakeable composition with the desired cationic activity, however the melting point was beyond the range of commercial feasibility and in the range where, after extended exposure to heat, the quat would begin to decompose. The second entry (B) includes an amount of glycol added to the solvent mixture. The resulting composition exhibited favorable cationic activity and melting point, but was not flakeable and thus is not included in the scope of the present invention. The third entry (C) was obtained by decreasing the amount of quat in relation to the solvent mixture (keeping the proportions of the solvent mixture constant) until the ending composition was flakeable. The resulting cationic activity was sufficient at 35.5%. The fourth entry (E) substituted cetyl alcohol for ceteryl alcohol in the solvent (in similar proportions). The resulting composition exhibited an extremely favorable cationic activity (49%) while still being flakeable and maintaining the commercially feasible handling properties.

The results of entry E tend to show that a composition including $C_{22}$ methosulfate quat and a solvent mixture of cetyl alcohol and butane diol provides an optimal composition for this specific system according to the present invention.

The fifth and sixth entries (F and G) show a $C_{22}$ chloride quat in a fatty alcohol solvent and in a fatty alcohol/glycol solvent. Again, entry G shows a preferred composition exhibiting the desired characteristics of a commercially feasible, flakeable composition with cationic activity greater than 35%.

What is claimed is:
1. A composition comprising:
    a solvent, said solvent including at least one fatty alcohol and at least one glycol, wherein the amount of said at least one fatty alcohol in said solvent is greater than the amount of said at least one glycol;
    a fatty ammonium monoalkyl quat distributed in said solvent;
    said fatty ammonium monoalkyl quat being present in an amount which is sufficient to provide at least 35% cationic activity,
    wherein said composition is flakeable, and has a melting point of less than 100° C.
2. The composition of claim 1, wherein said fatty ammonium monoalkyl quat is a fatty ammonium methyl quat.
3. The composition of claim 1, wherein said at least one fatty alcohol is a substantially homogeneous alcohol.
4. The composition of claim 1, having a melting point of less than 95° C.
5. The composition of claim 1, having a melting point of less than 90° C.

6. The composition of claim 1, wherein the amount of said at least one fatty alcohol in said solvent is at least 60% by weight.

7. A fatty ammonium quat composition, comprising:

a solvent including at least one fatty alcohol having a chain length of 12 to 24 carbons and at least one glycol, wherein the amount of said at least one fatty alcohol in said solvent is greater than the amount of said at least one glycol; and a fatty ammonium monoalkyl quat having at least one fatty chain of between about 12 and about 36 carbons in length, said fatty ammonium monoalkyl quat being distributed in said solvent;

said fatty ammonium monoalkyl quat, being present in an amount which is sufficient to provide at least 35% cationic activity, and wherein said fatty ammonium quat composition is flakeable and has a melting point of less than 100° C.

8. The fatty ammonium quat composition of claim 7, having a melting point of 95° C.

9. The fatty ammonium quat composition of claim 7, having a melting point of less than 90° C.

10. The fatty ammonium quat composition of claim 7, wherein said fatty ammonium monoalkyl quat is a behenyl, erucic, cetyl or stearyl fatty ammonium quat.

11. The fatty ammonium quat composition of claim 7, wherein said fatty ammonium monoalkyl quat is a fatty ammonium trimethyl quat.

12. The fatty ammonium quat composition of claim 7, wherein said at least one fatty alcohol is a lauryl, a myristal, a cetyl, a stearyl, a behenyl, or a cetearyl fatty alcohol.

13. The fatty ammonium quat composition of claim 7, wherein said at least one glycol is an ethylene glycol, a propylene glycol, a butylene glycol, a dipropylene glycol, a polypropylene glycol or a polyethylene glycol.

14. The fatty ammonium quat composition of claim 7, wherein the amount of said at least one fatty alcohol in said solvent is at least 60% by weight.

15. The fatty ammonium quat composition of claim 7, wherein the amount of said at least one fatty alcohol in said solvent is at least 75% by weight.

16. The fatty ammonium quat composition of claim 7, wherein the amount of said at least one fatty alcohol in said solvent is at least 90% by weight.

17. A composition comprising:

a solvent, said solvent including at least one fatty alcohol and at least one glycol wherein the amount of said at least one fatty alcohol in said solvent is greater than the amount of said at least one glycol;

a fatty ammonium monoalkyl quat distributed in said solvent;

said fatty ammonium monoalkyl quat being present in an amount which is sufficient to provide at least 35% cationic activity, wherein said composition is pastillatable and has a melting point less than 100° C.

18. The composition of claim 17, wherein said fatty ammonium monoalkyl quat is a fatty ammonium methyl quat.

19. The composition of claim 17, wherein said at least one fatty alcohol is a substantially homogeneous alcohol.

20. The composition of claim 17, wherein said at least one fatty alcohol has a chain length of 12 to 24 carbons.

21. The composition of claim 17, wherein said fatty ammonium monoalkyl quat has at least one fatty chain of between about 12 and about 36 carbons in length.

22. The composition of claim 17, having a melting point of less than 95° C.

23. The composition of claim 17, having a melting point of less than 90° C.

24. The composition of claim 17, wherein the amount of said at least one fatty alcohol in said solvent is at least 60% by weight.

25. The composition of claim 17, wherein the amount of said at least one fatty alcohol in said solvent is at least 75% by weight.

26. The composition of claim 17, wherein the amount of said at least one fatty alcohol in said solvent is at least 90% by weight.

27. The composition of claim 17, wherein said fatty ammonium monoalkyl quat is a behenyl, erucic, cetyl or stearyl fatty ammonium quat.

28. The composition of claim 17, wherein said fatty ammonium monoalkyl quat is a fatty ammonium trimethyl quat.

29. The composition of claim 17, wherein said at least one fatty alcohol is a lauryl, a myristal, a cetyl, a stearyl, a behenyl, or a cetearyl fatty alcohol.

30. The composition of claim 17, wherein said at least one glycol is an ethylene glycol, a propylene glycol, a butylene glycol, a dipropylene glycol, a polypropylene glycol or a polyethylene glycol.

* * * * *

UNITED STATES PATENT AND TRADEMARK OFFICE
CERTIFICATE OF CORRECTION

PATENT NO. : 6,607,715 B1  
DATED : August 19, 2003  
INVENTOR(S) : Helena S. Barinova, Kostas Nikolopoulos and Abel G. Pereira It is certified that error appears in the above-identified patent and that said Letters Patent is hereby corrected as shown below:

<u>Title page, Item [54] and Column 1, line 1,</u>  
Before "FATTY" insert -- NOVEL --.

<u>Column 4,</u>  
Line 56, "($C_{8:0}$)" should read -- $C_{18:0}$) --.

<u>Column 5,</u>  
Line 52, "$950^{\circ}$" should read -- $95^{\circ}$ --.

Signed and Sealed this

Sixth Day of January, 2004

JAMES E. ROGAN  
*Director of the United States Patent and Trademark Office*